United States Patent [19]

Taniguchi et al.

[11] Patent Number: 4,891,465

[45] Date of Patent: Jan. 2, 1990

[54] PROCESS FOR PRODUCTING ALKYL GROUP-SUBSTITUTED AROMATIC HYDROCARBONS

[75] Inventors: Katsuo Taniguchi; Michio Tanaka, both of Iwakuni; Kazunori Takahata, Hiroshima; Naoya Sakamoto, Ootake; Toshihiro Takai, Ootake; Yoshito Kurano, Iwakuni; Masayasu Ishibashi, Yamaguchi, all of Japan

[73] Assignee: Mitsui Petrochemical Industries, Ltd., Tokyo, Japan

[21] Appl. No.: 221,246

[22] PCT Filed: Nov. 10, 1987

[86] PCT No.: PCT/JP87/00864

§ 371 Date: Jul. 6, 1988

§ 102(e) Date: Jul. 6, 1988

[87] PCT Pub. No.: WO88/03523

PCT Pub. Date: May 19, 1988

[30] Foreign Application Priority Data

Nov. 11, 1986 [JP]  Japan .................. 61-268049

[51] Int. Cl.$^4$ .................................. C07C 2/70
[52] U.S. Cl. ........................... 585/463; 585/462
[58] Field of Search .................... 585/462, 463

[56] References Cited

U.S. PATENT DOCUMENTS

| | | | |
|---|---|---|---|
| 2,425,747 | 8/1947 | Lieber et al. | 585/462 |
| 2,584,103 | 3/1952 | Pines et al. | 585/463 |
| 3,248,442 | 4/1966 | Goble et al. | 585/463 |
| 3,251,897 | 5/1966 | Wise | 585/467 |
| 3,402,213 | 9/1968 | De Ross et al. | 585/463 |
| 3,417,148 | 12/1968 | Fishel | 585/463 |
| 4,530,756 | 7/1985 | Chang et al. | 585/463 |

*Primary Examiner*—Patrick P. Garvin
*Assistant Examiner*—E. D. Irzinski
*Attorney, Agent, or Firm*—Sherman and Shalloway

[57] ABSTRACT

In a process for producing an alkyl group-substituted aromatic hydrocarbon according to the present invention, (i) an aromatic hydrocarbon is reacted with (ii) an alkylating agent selected from the group consisting of olefins, lower aliphatic alcohols and alkyl halides in the presence of a mordenite-type zeolite catalyst treated with a fluorine-containing compound, and therefore the conversion of the aromatic compound can be increased and further it is possible to introduce the specific number of alkyl groups into the specific position of the aromatic compound.

In particular, when biphenyl is used as the aromatic hydrocarbon and propylene is used as the alkylating agent, p,p'-diisopropylbiphenyl can be obtained in a high yield and high selectivity.

16 Claims, No Drawings

PROCESS FOR PRODUCTING ALKYL GROUP-SUBSTITUTED AROMATIC HYDROCARBONS

TECHNICAL FIELD

This invention relates to a process for producing alkyl group-substituted aromatic hydrocarbons and, more particularly, to a process for producing alkyl group-substituted aromatic hydrocarbons by reacting an aromatic hydrocarbons with an alkylating agent such as an olefin in the presence of a specific catalyst.

BACKGROUND ART

Aromatic hydrocarbons having alkyl substituents are widely used in a variety of fields. For example, they are used as starting materials for polymers, as intermediates for dyes, drugs and agricultural chemicals, or as starting materials for liquid crystal polymers. It is well known that such aromatic compounds having alkyl substituents can be produced by reacting aromatic compounds with alkylating agents such as olefins and alcohols in the presence of catalysts such as alumina, silica-alumina and aluminum chloride.

However, when alkyl group-substituted aromatic hydrocarbons are intended to be produced by reacting certain aromatic compounds such as biphenyl and naphthalene with alkylating agents such as olefins in the presence of well known catalysts such as silica-alumina and aluminum chloride, the conversion of the aromatic compounds may be low or it is usually difficult to introduce the specific number of alkyl substituents into specific positions of the aromatic compounds.

For example, when dialkylbiphenyls used in the production of biphenols useful as starting materials for condensation polymers are intended to be obtained by reacting biphenyl with alkylating agents such as olefins, it is necessary to produce dialkylbiphenyls, particularly p,p'-dialkylbiphenyl from biphenyl in a good yield. However, catalysts capable of producing dialkylbiphenyls, particularly p,p'-dialkylbiphenyl from biphenyl in a good yield are not yet known.

Japanese Patent Publn. No. 3298/1967 discloses a process for alkylating an aromatic compound which comprises the step of reacting aromatic compounds or an aromatic compound having non-polar substituents with alkylating agents such as olefins, alkyl halides and alcohols at a temperature of no more than 315° C. in the presence of aluminosilicate catalysts such as Zeolite X, zeolite Y and mordenite. According to this reference, benzene and naphthalene are used as the aromatic compounds to be alkylated in examples, and said reference teaches that Zeolite X ion exchanged by rare earth metals exhibits particularly high activity among the aluminosilicate catalysts used in alkylating such aromatic compounds. However, we have found that in case that biphenyl is reacted with the alkylating agents such as olefins in the presence of the catalysts such as silica-alumina, the ion exchanged Zeolite X by rare earth metals, Zeolite Y and hydrogen-type Zeolite X disclosed in Japanese Patent Publn. No. 3298/1967, the conversion of biphenyl is low and further the selectivity of p,p'-dialkylbiphenyl is also low.

In view of the facts as described above, we have carried out studies in order to find out catalysts which produce an alkyl group-substituted aromatic compound by reacting an aromatic compound with an alkylating agent such as an olefin, and increase the conversion of the aromatic compound and which can introduce the specific number of alkyl substituents into specific positions of the aromatic compound. We have now found that the advantages described above can be obtained by a specific catalyst. The present invention has been completed on the basis of such a discovery.

An object of the present invention is to provide a process for producing an alkyl group-substituted aromatic hydrocarbon comprising reacting an aromatic compound with an alkylating agent such as an olefin in the presence of a specific catalyst which are intended to solve the problems associated with the prior art with the increased conversion of the aromatic compound and which can introduce the specific number of alkyl groups into the specific positions of the aromatic compound.

DISCLOSURE OF INVENTION

A process for producing an alkyl group-substituted aromatic hydrocarbon according to the present invention comprises the step of reacting (i) an aromatic hydrocarbon with (ii) an alkylating agent selected from the group consisting of olefins, aliphatic lower alcohols and alkyl halides in the presence of a mordenite-type zeolite catalyst treated with a fluorine-containing compound.

In the process for producing the alkyl group-substituted aromatic hydrocarbon according to the present invention, (i) the aromatic hydrocarbon is reacted with (ii) the alkylating agent selected from the group consisting of olefins, aliphatic lower alcohols and alkyl halides in the presence of the mordenite-type zeolite catalyst treated with the fluorine-containing compound, and therefore the conversion of the aromatic compound can be increased and further it is possible to introduce the specific number of the alkyl groups into the specific positions of the aromatic compound.

BEST MODE FOR CARRYING OUT THE INVENTION

A process for producing an alkyl group-substituted aromatic hydrocarbon according to the present invention will be described in detail.

AROMATIC HYDROCARBON

Examples of aromatic hydrocarbons which are used in the present invention include benzene; monoalkyl benzenes such as toluene, ethylbenzene and isopropylbenzene; biphenyl and biphenyls having one or two substituents such as methyl, ethyl, isopropyl, phenyl, chloro, methoxy and acetyl; naphthalene and naphthalenes having one or more substituents such as methyl, ethyl, isopropyl, methoxy, acetyl and halogens; diphenyl ether and diphenyl ethers having one or more substituents such as methyl, ethyl, isopropyl, halogens, methoxy and acetyl; diphenylmethane, diphenylethane, diphenylpropane and diphenylalkanes having one or more substituents such as methyl, ethyl, propyl, halogens and acetyl. Of these, a particularly preferred aromatic hydrocarbon is biphenyl. When biphenyl is used to carry out the reaction according to the present invention, the conversion of biphenyl can be increased, as well as p,p'-dialkylbiphenyls which are compounds having the specific number of alkyl groups introduced into the specific positions of biphenyl can be obtained in a high yield and high selectivity.

ALKYLATING AGENT

An alkylating agent for alkylating the aromatic hydrocarbon as described above in the present invention is selected from the group consisting of olefins, aliphatic lower alcohols and alkyl halides.

Examples of olefins which are used as the alkylating agent include ethylene, propylene, n-butene, isobutene, octene, decene, cyclopentene, cyclohexene, and isoamylene. Examples of the aliphatic alcohols for use herein include ethanol, propanol, n-butanol, isobutanol, tertiary-butanol, cyclopentanol, cyclohexanol and dodecyl alcohol. Examples of the alkyl halides for use herein include methyl chloride, methyl iodide, ethyl chloride, ethyl iodide, propyl chloride, propyl iodide, dodecyl chloride, butyl chloride, benzyl chloride and chlorotoluene.

CATALYST

In the present invention, in carrying out the reaction of the aromatic hydrocarbon with the alkylating agent as described above, a mordenite-type zeolite catalyst treated with a fluorine-containing compound is used. While hydrogen ion-exchanged mordenite-type zeolites are particularly preferably used as the starting mordenite-type zeolite materials which will be treated with the fluorine-containing compound, ion-exchanged mordenite-type zeolites with metal ions such as rare earth metals, transition metals and alkaline earth metals can be optionally used as the starting materials.

In order to treat the mordenite-type zeolites as described above with the fluorine-containing compound, the following methods can be utilized:

(a) A method wherein a mordenite-type zeolite is immersed in a solution of a fluorine-containing compound such as 5-20 weight % aqueous hydrofluoric acid or an aqueous ammonium fluoride solution, for example for from 2 to 10 hours and thereafter the impregnated mordenite-type zeolite is fired in air or in an inert gas atmosphere such as nitrogen.

(b) A method wherein a mordenite-type zeolite is brought into contact with a gaseous fluorine-containing compound such as $CFCl_3$, $CF_2Cl_2$, $CF_3Cl$, $CF_4$, $CHFCl_2$, $CHF_2Cl$, $CHF_3$, $CFCl_2$—$CFCl_2$, $CF_2Cl$—$CF_2Cl$, $CF_2Cl$—$CF_3$, $CF_3$—$CF_3$, $CH_3$—$CF_2Cl$, $CH_3$—$CHF_2$, $(CF_2$—$CF_2)_2$, $CF_3Br$, $CF_2Br$—$CF_2Br$, HF, $SF_4$, $SF_6$ or $BF_3$ at a temperature of from 250° C. to 800° C., preferably from 300° C. to 600° C.

For example, a reaction tube is packed with the mordenite-type zeolite; the reaction tube is then heated to a predetermined temperature; the gaseous fluorine-containing compound as described above is fed to the reaction tube described above over a predetermined time of period (e.g., from 0.1 to 10 hours, preferably from 0.5 to 2 hours) to contact the mordenite-type zeolite with the gaseous fluorine-containing compound as described above; and thereafter the fluorine-containing compound remaining in the reaction tube may be optionally substituted with an inert gas such as nitrogen or removed by subjecting it to evacuating treatment under reduced pressure.

A mordenite-type zeolite treated with the fluorine-containing compound is reported in Japanese Laid-Open publn. No. 155139/1985, Catalyst 25, (2), 103(1983), J. Chem. Soc. Faraday. Trans. I 1985,81,1161 and the like. However, the literature described above does not teach that the mordenite-type zeolite treated with the fluorine-containing compound can be used as a specific catalyst for the reaction of an aromatic hydrocarbon with an alkylating agent such as an olefin.

REACTION CONDITIONS

The reaction of an aromatic hydrocarbon with an alkylating reaction using the mordenite-type zeolite catalyst treated with the fluorine-containing compound according to the present invention may be carried out in a gas phase reaction or in a liquid phase reaction.

In case that the reaction according to the present invention is carried out in the gas phase reaction, the reaction pressure may be atmospheric pressure or superatmospheric pressure. It is desirable that the reaction is carried out under pressure. The reaction pressure is preferably from 3 to 100 kg/cm$^2$G, and the reaction temperature is from 150° to 350° C., preferable from 200° to 250° C. LHSV is from 0.05 to 5 hr$^{-1}$, preferably from 0.1 to 1.0 hr$^{-1}$, and the molar ratio of the aromatic hydrocarbon to the alkylating agent is from 1:2 to 1:20, preferably from 1:3 to 1:10. In carrying out the reaction according to the present invention in the gas phase reaction, the aromatic hydrocarbon can be fed to a reaction system together with a diluent. Examples of such diluents which can be used include n-decane, n-dodecane, dichlorobenzene and nitrobenzene.

In case that the reaction according to the present invention is carried out in the liquid phase reaction, the reaction pressure may be atmospheric pressure or superatmospheric pressure. It is desirable that the reaction is carried out under pressure. The reaction pressure is preferably from 3 to 100 kg/cm$^2$G. In carrying out the reaction, a solvent may be used, and optionally no solvent may be used. The reaction temperature is from 100° C. to 300° C., preferably from 150° C. to 250° C. The molar ratio of the aromatic hydrocarbon to the alkylating agent is from 1:2 to 1:20, preferably 1:3 to 1:10.

When the reaction according to the present invention is carried out in the liquid phase reaction using a solvent, a solvent such as n-decane, n-dodecane, n-tridecane, decalin, dichlorobenzene, nitrobenzene or the like can be used.

As described above, in case that the reaction of the aromatic hydrocarbon, particularly biphenyl with the alkylating agent according to the present invention is carried out in the presence of the mordenite-type zeolite catalyst treated with the fluorine-containing compound, particularly hydrogen ion-exchanged mordenite-type zeolite catalyst treated with the fluorine-containing compound, under pressure, the aromatic hydrocarbon is reacted in a high conversion as well as p,p'-dialkylbiphenyl is formed in a high selectivity. On the contrary, when zeolites other than mordenite-type zeolite, e.g., hydrogen ion-exchanged Zeolite X, hydrogen ion-exchanged Zeolite Y, and solid acids such as silica alumina and aluminum chloride are used as the catalyst, the conversion of biphenyls is remarkably reduced and a large amount of a monoalkylbiphenyl is formed. Accordingly, the selectivity of p,p'-dialkylbiphenyl is remarkably reduced. When a mordenite-type zeolite which is not treated with a fluorine-containing compound is used as a catalyst, the conversion of biphenyls cannot be increased and the selectivity of p,p'-dialkylbiphenyl cannot be increased. For example, in case that the reaction of biphenyls with propylene is carried out in the liquid phase reaction in the presence of the hydrogen ion-exchanged mordenite zeolite catalyst treated with the fluorine-containing compound at a reaction temperature of 250° C. under a pressure of 20 kg/cm²G, the conversion of biphenyls is 58%, and the selectivity of diisopropylbiphenyls is 58%, and the selectivity of p,p'-diisopropylbiphenyl (4,4'-diisopropylbiphenyl) to the total isomers of diisopropyl biphenyls is 84%. On the contrary, in case that the reaction of biphenyls with propylene is carried out in the liquid phase reaction in the presence of the hydrogen ion-exchanged Zeolite Y catalyst at a reaction temperature of 250° C. under a pressure of 7 kg/cm²G, the conversion of biphenyls is 56.1% and the selectivity of p,p'-diisopropylbiphenyl among the resulting diisopropylbiphenyls is as low as 23.5%.

The thus obtained 4,4'-diisopropylbiphenyl is oxidized with molecular oxygen to form 4,4'diisopropylbiphenyl dihydroperoxide and this 4,4'-diisopropylbiphenyl dihydroperoxide is subjected to acid decomposition to obtain 4,4'-dihydroxybiphenyl.

In case that 4,4'-dihydroxybiphenyl is produced by oxidizing 4,4'-diisopropylbiphenyl with molecular oxygen to form 4,4'-diisopropylbiphenyl dihydroxyperoxide and then acid decomposing this 4,4'-diisopropylbiphenyl dihydroxyperoxide, a large amount of 4,4'-dihydroxybiphenyl can be efficiently produced from 4,4'-diisopropylbiphenyl.

A process for producing 4,4'-dihydroxybiphenyl from 4,4'-diisopropylbiphenyl will be described.

OXIDATION REACTION 4,4'-Diisopropylbiphenyl is used as a starting material to produce 4,4'-dihydroxybiphenyl, and this 4,4'-diisopropylbiphenyl is oxidized with molecular oxygen to form 4,4'-diisopropylbiphenyl dihydroperoxide.

Such an oxidation reaction of 4,4'-diisopropylbiphenyl is preferably carried out in the presence of a base. For example, the oxidation reaction is carried out by adding 4,4'-diisopropylbiphenyl to an aqueous solution of a base, mechanically mixing them to form an emulsion and flowing a gas containing molecular oxygen into the emulsion.

In carrying out the oxidation as described above, the aqueous solution of the base is not necessarily used, however, in the following description, the oxidation reaction is carried out in the presence of the aqueous solution of the base.

In case that the oxidation is carried out in the presence of the aqueous solution of the base, an alkali metal compound is preferably used as the base. Examples of such alkali metal compounds include sodium hydroxide, potassium hydroxide, sodium carbonate, potassium carbonate, potassium acetate, sodium nitrate, and potassium phosphate. Of these, potassium acetate, sodium acetate, potassium carbonate and sodium hydroxide are preferred. The concentration of these alkali metal compounds in the aqueous solution is preferably no more than 20% by weight.

The amount of the aqueous base solution used in the reaction mixture usually comprises from 5% to 80% by weight of the reaction mixture, particularly preferably within the range of from 20% to 70% by weight. If the amount of the aqueous base solution used is less than 5% by weight of the reaction mixture, the dispersion state of the reaction solution containing oily unreacted 4,4'-diisopropylbiphenyl, oxidation products thereof and the aqueous base solution becomes poor, and therefore the emulsion state becomes insufficient to adversely affect the oxidation reaction. Thus, the use of less than 5% by weight of the aqueous base solution is not preferably. If the amount of the aqueous base solution used is more than 80% by weight, the emulsion state of the reaction system will become poor. Thus, the use of more than 80% by weight of the aqueous base solution is not preferable Further, it is desirable that the pH of the reaction system is from 8 to 14, preferably from 10 to 13.6.

While 4,4'-diisopropylbiphenyl, oxidation products thereof and the aqueous base solution can be usually emulsified throughly by mechanical stirring, they may be optionally stirred in the presence of known emulsifier such as stearic acid.

Alkaline earth metal hydroxides such as calcium hydroxide, magnesium hydroxide and strontium hydroxide can be used as the base described above. Of these, calcium hydroxide is particularly preferred. These alkaline earth metal hydroxides may be used alone or may be used in combination with the alkali metal compounds described above.

While pure oxygen gas may be used as the molecular oxygen, usually air is sufficient. The amount of the molecular oxygen required is usually within the range of from 1 to 15 Nl/hour, preferably from 2 to 10 Nl/hour (on a oxygen gas basis) per 100 grams of 4,4'-diisopropylbiphenyl charged for oxidation reaction, it is not restricted to these amounts.

The reaction temperature is usually from 80° to 150° C., preferably from 90° C. to 130° C. While the reaction time can vary depending upon conditions such as reaction temperature, it is usually from 6 to 40 hours. While the reaction is normally carried out under atmospheric pressure, it can be carried out under pressure or under reduced pressure as needed.

In the oxidation reaction of 4,4'-diisopropylbiphenyl, a reaction initiator is preferably used. For example, compounds such as α,α-azobis (cyclohexane-1-carbonitrile) can be used as the reaction initiator. The induction period of the reaction can be reduced by using the reaction initiator. The amount of the reaction initiator used is usually within the range of from 0.005–1 part by weight per 100 parts by weight of the charged reaction mixture containing the starting material 4,4'-diisopropylbiphenyl.

Thus, when the oxidation reaction of 4,4'-diisopropylbiphenyl is carried out, various by-products are formed in addition to 4,4'-diisopropylbiphenyl dihydroxyperoxide (DHP). These are shown in Table 1-A.

TABLE 1-A

| Structure | Abbreviation | structure | Abbreviation |
|---|---|---|---|
| 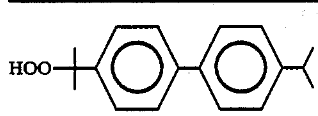 | MHP | 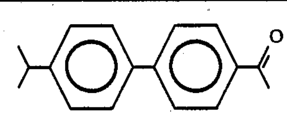 | MK |

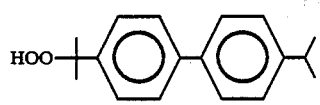

TABLE 1-A-continued

| Structure | Abbreviation | Structure | Abbreviation |
|---|---|---|---|
| HO—⟨phenyl⟩—⟨phenyl⟩—⟨ | MC | HO—⟨phenyl⟩—⟨phenyl⟩—C(=O)— | KC |
| HOO—⟨phenyl⟩—⟨phenyl⟩—OOH | DHP | HOO—⟨phenyl⟩—⟨phenyl⟩—C(=O)— | KHP |
| HOO—⟨phenyl⟩—⟨phenyl⟩—OH | HHP | (O=)C—⟨phenyl⟩—⟨phenyl⟩—C(=O) | DK |
| HO—⟨phenyl⟩—⟨phenyl⟩—OH | DC | | |

Amounts of the unreacted 4,4'-diisopropylbiphenyl and the oxidation reaction products such as the MHP, HHP, DC, MHP, and MC can be determined by separating an organic phase and an aqueous phase after reaction, extracting this aqueous phase with ether or the like, and then analyzing the organic phase and the ether extract by means of liquid chromatography.

ACID CLEAVAGE REACTION

In case that 4,4'-diisopropylbiphenyl dihydroperoxide contained in the oxidation reaction mixture obtained as mentioned above is subjected to acid cleavage in the presence of an acid catalyst, acid cleavage reaction products containing 4,4'-dihydroxybiphenyl are obtained. Since carbinols are also contained in the oxidation reaction mixture as by-products, the HHP and PC among the carbinols which are by-products are oxidized with a hydrogen peroxide by adding the hydrogen peroxide in the oxidation reaction mixture to form dihydroperoxides and these hydroperoxides thus formed are simultaneously acid decomposed with the acid catalyst, 4,4'-dihydroxybiphenyl can be obtained in a high yield. Thus, the use of such a method is preferred.

In case that the conversion of 4,4'-diisopropylbiphenyl is increased to at least 80%, the yield of HHP and DC is increased in addition to the yield of MHP. If a method that the hydrogen peroxide is added to the oxidation reaction mixture when carring out the cleavage reaction is utilized, the HHP and DC can be converted to the DHP, and therefore 4,4'-dihydroxybiphenyl can be obtained in a high yield. Further, in this case, the yield of KHP which does not contribute to the formation of 4,4'-dihydroxybiphenyl can be reduced, and therefore the use of such a method is preferred. In particular, the yield of 4,4'-dihydroxybiphenyl can be enhanced by increasing the conversion of 4,4'-diisopropylbiphenyl to at least 90%, more preferably at least 95%.

Examples of the above hydrogen peroxide which can be used include hydrogen peroxide, an aqueous solution of hydrogen peroxide, and materials which generate hydrogen peroxide under reaction conditions, for example, such as sodium peroxide and calcium peroxide. It is preferable to use the aqueous solution of hydrogen peroxide. Desired 4,4'-dihydroxybiphenyl can be obtained in a high yield by using from 1.0 to 2 moles, preferably from 1.0 to 1.5 mole of hydrogen peroxide per mole of alcoholic hydroxyl group of the carbinols described above contained in the acid decomposition reaction. Further, the use of hydrogen peroxide under such conditions is also preferable because the formation of by-products attributable to the condensation of the carbinols can be remarkably inhibited at the same time.

Preferred acid catalysts used in the acid decomposition reaction include inorganic acids such as sulfuric acid, hydrochloric acid, nitric acid and phosphoric acid; solid acids such as strongly acidic ion exchange resins, silica gel and silica alumina; organic acids such as chloroacetic acid, methanesulfonic acid, benzenesulfonic acid and toluenesulfonic acid; heteropolyacids such as phosphorus wolframate and phosphorus molybdate. The acid catalyst may be added to the reaction system as it is. Alternatively, when the acid catalyst has solubility, it can be dissolved in a suitable inert solvent and added to the reaction system. While the amount of the acid catalyst used depends upon its types and reaction conditions, it is usually within the range of from 0.01 to 10% by weight based on the total reaction mixture.

The following procedure is practically advantageous. After the oxidation reaction of 4,4'-diisopropylbiphenyl, 4,4'-diisopropylbiphenyl dihydroxyperoxide and by-products are transferred from the reaction mixture to an organic solvent such as methyl isobutyl ketone, and this organic solvent is used as a reaction solvent to carry out the acid decomposition reaction. However, the reaction solvent is not restricted to methyl isobutyl ketone, and other inert organic solvents, for example, ketones such as acetone and methyl ethyl ketone; alcohols such as methanol and ethanol; lower aliphatic carboxylic acids such as acetic acid and propionic acid; and hydrocarbons such as benzene, toluene, xylene, hexane and heptane can be used. These mixtures can also be used.

This acid decomposition reaction is carried out at a temperature within the range of from 40° to 100° C., preferably from 60° to 80° C. This acid decomposition reaction is usually carried out for from 1 to 10 hours.

While the thus obtained dihydroxybiphenyl can be recovered from the reaction mixture by any conventional method, diacyloxybiphenyl can be recovered from dihydroxybiphenyl by the following procedure.

The oxidation reaction product containing diisopropylbiphenyl dihydroperoxide obtained by oxidizing diisopropylbiphenyl with molecular oxygen in the presence of the base is acid decomposed; an acylating agent is added to the resulting acid decomposition product containing the dihydroxybiphenyl to react dihydroxybiphenyl with the acylating agent in the presence of a catalyst; and the resulting diacyloxybiphenyl is separated from the reaction mixture.

Thus, when the oxidation reaction product containing diisopropylbiphenyl diihydroperoxide obtained by oxidizing diisopropylbiphenyl with molecular oxygen in the presence of the base is acid decomposed, the acylating agent is added to the acid decomposition product containing the resulting dihydroxybiphenyl to react dihydroxybiphenyl with the acylating agent in the presence of the acid catalyst and the resulting diacyloxybiphenyl is separated from the reaction mixture, highly pure diacyloxybiphenyl can be produced in a high yield as well as the process steps of diacyloxybiphenyl can be simplified.

A process for producing diacyloxybiphenyl will be described.

PRODUCTION OF DIACYLOXYBIPHENYL

Diacyloxybiphenyl is produced by adding an acylating agent to the acid decomposition reaction mixture containing dihydroxybiphenyl obtained as described above to react dihydroxybiphenyl with the acylating agent in the presence of the catalyst. In this case, in carrying out the acyloxylation reaction, a suitable amount of low boiling by-products such as acetone and reaction solvents may be optionally removed from the acid decomposition reaction mixture by distillation or the like.

It is preferred that the acylating agent is added in an amount of from 1 to 20 moles, preferable from 2 to 5 moles per mole of dihydroxybiphenyl contained in the acid decomposition reaction product.

Examples of such acylating agents for use herein include lower aliphatic carboxylic acid anhydrides such as formic anhydride, acetic anhydride, propionic anhydride, butyric anhydride and valeric anhydride; aromatic carboxylic acid anhydrides such as benzoic anhydride and toluic anhydride: and acid chlorides such as acetyl chloride.

The catalysts used in the reaction of dihydroxybiphenyl with the acylating agent can be similar to the acid catalysts used in the decomposition of diisopropylbiphenyl dihydroperoxide. Inorganic acids such as sulfuric acid, hydrochloric acid, phosphoric acid, and boron fluoride are particularly preferably used. Ion exchange resins which are solid acids can also be used. Bases can be used as catalysts in addition to the acids. Organic bases such as pyridine and quinoline as well as salts such as sodium acetate can be preferably used. While the amount of the catalyst used can vary depending upon its types and reaction conditions employed, it is usually within the range of from 0.01% to 10% by weight based on the total reaction mixture.

The reaction of dihydroxybiphenyl with the acylating agent such as carboxylic acid anhydride is carried out at a temperature within the range of from 0° to 200° C., preferably from 80° to 140° C. The reaction time is from 30 minutes to 5 hours, preferably about 1 to about 2 hours.

When the acylating agent such as carboxylic acid anhydride is added to the acid decomposition reaction product containing dihydroxybiphenyl as described above to react dihydroxybiphenyl with the acylating agent such as carboxylic acid anhydride followed by cooling of the resulting reaction mixture by allowing it to stand or the like, diacyloxybiphenyl is obtained as a precipitate from the reaction mixture.

The acid decomposition reaction can be carried out in the presence of a solvent selected from aromatic hydrocarbons such as cumene; dialkyl ketones such as methyl isobutyl ketone; and carboxylic acids. When methyl isobutyl ketone is used as the solvent to carry out the acyloxylation, impurities are extracted and remain in the solvent in separating the desired product diacyloxybiphenyl from the reaction mixture, and therefore the purity of the resulting diacyloxybiphenyl is increased. Thus, the use of methyl isobutyl ketone as the solvent is preferred.

Examples of the diacyloxybiphenyls include various substituted products such as 4,4'-diacyloxybiphenyl, 3,4'-diacyloxybiphenyl and 2,4'-diacyloxybiphenyl. The acyloxy group of said compounds is a group represented by the general formula:

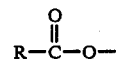

wherein R represents a lower alkyl group or an aryl group. Examples of such acyloxy groups include formyloxy, acetoxy, propionyloxy, butyryloxy, valeryloxy, benzoyloxy, and toluyloxy. Of these, acetoxy is preferred. Preferred diacyloxybiphenyls are 4,4'-diacyloxybiphenyl, 3,4'-diacyloxybiphenyl.

The thus obtained diacyloxybiphenyl has an extremely good purity of at least 99%, and the reaction yield of the diacyloxybiphenyl (on a dihydroxybiphenyl basis) also is extremely good (99 mole %). Further, the crystal recovery yield of the diacyloxybiphenyl also is good (95 mole %).

If another method is used to separate and purify dihydroxybiphenyl from the acid decomposition reaction product obtained by the oxidation of diisopropylbiphenyl and the subsequent acid decomposition, the recovery yield is about 90% and the purity of the resulting crystal is about 95%.

Thus, even when the diacyloxybiphenyl is produced by directly adding the acylating agent to the acid decomposition reaction product to react the dihydroxybiphenyl with the acylating agent without separating the dihydroxybiphenyl from the acid decomposition reaction product, diacyloxybiphenyl can be obtained in a high yield and high recovery as well as the process can be simplified as compared with a process wherein the dihydroxybiphenyl described above is separated from the acid decomposition reaction product and acyloxylated to obtain diacyloxybiphenyl.

Dihydroxybiphenyl can be readily obtained by hydrolyzing the thus obtained diacyloxybiphenyl with an acid or alkali as needed.

EFFECTS OF THE INVENTION

In the process for producing the alkyl group-substituted aromatic hydrocarbon according to the present invention, (i) the aromatic hydrocarbon is reacted with (ii) the alkylating agent selected from the group consisting of olefins, aliphatic lower alcohols and alkyl halides in the presence of the mordenite-type zeolite catalyst treated with the fluorine-containing compound and therefore the conversion of the aromatic compound can be increased and further it is possible to introduce the specific number of alkyl groups into the specific positions of the aromatic compound.

While the present invention is illustrated by the following examples, the present invention is not limited to there examples.

EXAMPLE 1

Preparation of Catalyst 30 grams of a powdered hydrogen ion-exchanged mordenite-type zeolite (hereinafter referred to as HM; manufactured by Shokubai Kasei Kogyo) were added to 50 milliliters of a 10 weight % aqueous $NH_4F$ solution, and the mixture was stirred for one hour at a temperature of 50° C. The mixture was filtered off, dried for 12 hours at a temperature of 100° C., and calcinated for further 3 hours at a temperature of 600° C. to obtain a hydrogen ion-exchanged mordenite-type zeolite catalyst treated with the fluorine-containing compound (hereinafter referred to as FHM-01).

The F content contained in this catalyst was analyzed to be 0.27% by weight (on a dry basis) by oxygen-flask-burning method. The crystal structure was examined by the XRD, and it was confirmed that the crystal structure of HM was maintained.

EXAMPLE 2

Preparation of Catalyst

Various FHM catalysts were prepared in the same manner as that described in Example 1 except that the time required for treating with the 10 weight % aqueous $NH_4F$ solution was changed to 3, 6 or 9 hours. The catalyst obtained when the treatment time was 3 hours was referred to as FHM-02, and the catalysts obtained when the treatment times were 6 and 9 hours were referred to as FHM-03 and FHM-04, respectively.

The resulting fluorine content was shown in Table 1-B.

TABLE 1-B

| catalyst No. | (FHM-) | 02 | 03 | 04 |
|---|---|---|---|---|
| Treatment Time | (hr) | 3 | 6 | 9 |
| F content | (wt %) | 0.91 | 2.81 | 3.68 |

EXAMPLE 3

Preparation of Catalyst

A commercially available Freon gas $CF_3Cl$ was used as a fluorine-containing compound with which a mordenite-type zeolite is treated and a FHM catalyst was prepared as follows: A quartz reaction tube having an inside diameter of 30 millimeters was packed with 20 grams of a granular hydrogen ion-exchanged mordenite (HM), and the HM was treated for 3 hours at a temperature of 600° C. in a stream of an $N_2$ gas. Thereafter, the temperature was set at 450° C., and a $CF_3Cl$ gas was passed at a flow rate of 8 milliliters per minute whereupon an $N_2$ gas was passed as a diluent at a flow rate of 92 milliliters per minute. After one hour, the introduction of the $CF_3Cl$ gas was stopped and thereafter the resulting mass was treated for 2 hours at a temperature of 600° C. in a stream of an $N_2$ gas to obtain a hydrogen ion-exchanged mordenite-type zeolite catalyst. (FHM-11)

The F content of this catalyst was 1.8% by weight, and the crystal structure was similar to that of the untreated hydrogen ion-exchanged mordenite-type zeolite.

EXAMPLE 4

Preparation of Catalyst $SF_6$ was used as a fluorine-containing compound with which a mordenite-type zeolite is treated and a FHM catalyst was prepared as follows: A quartz reaction tube having an inside diameter of 30 millimeters was packed with 20 grams of a granular hydrogen ion-exchanged mordenite (HM), and evacuated for one hour at a temperature of 600° C. $SF_6$ was introduced at about room temperature up to one atmosphere, and maintained for one hour while warming to 550° C. Thereafter, evacuation was carried out for one hours at a temperature of 600° C., to obtain a $SF_6$-treated hydrogen ion-changed mordenite-type zeolite catalyst. (FHM-21)

The F content of this catalyst was 3.20% by weight, and its crystal structure was similar to that of the untreated hydrogen ion-exchnged mordenite-type zeolite. It was recognized that a minor amount of $AlF_3$ was present by the XRD.

EXAMPLE 5

Reaction Example

FHM-01 prepared in Example 1 was used as a catalyst to carry out the isopropylation reaction of biphenyl.

A 100 milliliter SUS autoclave equipped with a rotatable stirrer was charged with 10 grams of biphenyl, 1.0 grams of the FHM-01 catalyst and 10 grams of tridecane as a solvent, and thereafter propylene was introduced at a temperature of 250° C. The total pressure was maintained at 20 kg/cm$^2$, and stirring was continued for 2.5 hours. After reaction was completed, the catalyst was filtered off, and the reaction solution was analyzed by means of gas chromatography. The reaction results were calculated.

The results are shown in Table 2.

EXAMPLE 6–10

Reaction Example

The isopropylation of biphenyl was carried out as in Example 5 except that the FHM catalysts prepared in Examples 2, 3 and 4 were used.

The results are shown in Table 2.

COMPARATIVE EXAMPLE 1

The isopropylation reaction of biphenyl was carried out as in Example 5 except that a hydrogen ion-exchanged mordenite zeolite (HM available from Shokubai Kasei Kogyo) was used as a catalyst as it is.

The results are shown in Table 2.

COMPARATIVE EXAMPLE 2–3

The isopropylation of biphenyl was carried out as in Example 5 except that a hydrogen ion-exchanged zeolite X (HY; comparative Example 2) and $AlCl_3$ (Comparative Example 3) were used as a catalyst and the reaction pressure was changed to 7 kg/cm$^2$.

The results are shown in Table 2.

TABLE 2

| Catalyst | Example 5 FHM-01 | Example 6 FHM-02 | Example 7 FHM-03 | Example 8 FHM-04 | Example 9 FHM-11 | Example 10 FHM-21 | Comparative Example 1 HM—O | Comparative Example 2 HY | Comparative Example 3 AlCl$_3$ |
|---|---|---|---|---|---|---|---|---|---|
| Conversion of biphenyl (%) | 57.6 | 69.5 | 55.5 | 59.8 | 60.2 | 65.1 | 37.0 | 56.1 | 60.0 |
| Selectivity of products (%) | | | | | | | | | |
| Monoalkyl products | 40.6 | 38.5 | 42.9 | 41.4 | 40.5 | 38.1 | 68.8 | 61.7 | 34 |
| Dialkyl products | 57.7 | 60.1 | 56.1 | 57.5 | 58.5 | 61.1 | 31.0 | 33.5 | 35.2 |
| Trialkyl products and other products | 1.7 | 1.4 | 0.9 | 1.1 | 1.0 | 0.8 | 0.5 | 4.8 | 29.7 |
| Selectivity of position | | | | | | | | | |
| $\frac{p,p'\text{-Isomer}}{\text{Dialkyl bialkylated products}} \times 100$ | 83.9 | 79.3 | 83.5 | 80.9 | 84.0 | 86.3 | 78.5 | 23.5 | 3.0 |

EXAMPLE 11

The fluorine-treated H-type mordenite FHM-02 prepared in Example 2 was used as a catalyst to carry out the isopropylation reaction of naphthalene as follows:

A 100 milliliter SUS autoclave equipped with a rotatable stirrer was charged with 10 grams of naphthalene, 1.0 gram of the FHM-02 catalyst and 10 grams of tridecane as a solvent, and thereafter propylene was introduced at a temperature of 250° C. The total pressure was maintained at 20 kg/cm$^2$, and stirring was continued for 5 hours. After the reaction was completed, the catalyst was separated and the reaction solution was analyzed by means of gas chromatography. The reaction results were calculated.

The results are shown in Table 3.

EXAMPLE 12

Example 11 was repeated except that the H-type mordenite FHM-01 obtained by ion exchanging with NH$_4$F, prepared in Example 1 was used as a catalyst, the amount of the catalyst was changed from 1.0 gram to 0.5 gram, and the stirring rate was changed from 500 rpm to 700 rpm.

The results are shown in Table 3.

COMPARATIVE EXAMPLE 4

The isopropylation reaction of naphthalene was carried out in the same manner as that described in Example 11 except that a hydrogen-exchanged mordenite not to be treated with fluorine was used as a catalyst.

The results are shown in Table 3.

TABLE 3

| Catalyst | Example 11 FHM-02 | Example 12 FHM-01 | Comparative Example 4 HM |
|---|---|---|---|
| Conversion of naphthalene (%) | 62.3 | 68.9 | 42.6 |
| Selectivity of products (%) | | | |
| Monoalkyl products | 42.2 | 56.1 | 80.3 |
| Dialkyl products | 55.6 | 40.8 | 17.2 |
| Trialkyl products | 2.2 | 3.0 | 2.5 |
| $\frac{\beta,\beta'\text{-Isomer*}}{\text{Dialkyl products}} \times 100$ | 88 | 85 | 76 |

*(2,6-diisopropylnaphthalene + 2,7-diisopropylnaphthalene)

EXAMPLE 13

The fluorine-treated H-type mordenite prepared in Example 1 was used and the alkylation reaction of diphenylmethane shown below by propylene was carried out as follows:

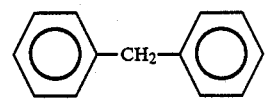

Ten grams of diphenylmethane, 0.5 gram of the catalyst and 10 grams of tridecane as a solvent were charged in an autoclave, and propylene was introduced untile the total pressure became about 20 kg/cm$^2$G at room temperature. The temperature was raised to 250° C., and the reaction mixture was stirred at 700 rpm to carry out the reaction for 5 hours.

The results are shown in Table 4.

COMPARATIVE EXAMPLE 5

The isopropylation reaction of diphenylmethane was carried out as in Example 13 except that the fluorine-treated H-type mordenite was replaced with a commercially available H-type mordenite (TSZ-620 available from Toyo Soda) as a catalyst.

The results are shown in Table 4.

TABLE 4

| | Examples 13 | Comparative Example 5 |
|---|---|---|
| Catalyst | F-treated H-mordenite | H-mordenite |
| Conversion of diphenylmethane (%) | 70.5 | 71.3 |
| Composition of product (mole %) | | |
| Monoisopropyldiphenylmethane | 42.9 | 66.4 |
| Diisopropyldiphenylmethane | 55.9 | 32.3 |
| Triisopropyldiphenylmethane | 1.1 | 1.3 |

EXAMPLE 14

The fluorine-treated H-type mordenite prepared in Example 1, and the alkylation reaction of diphenyl ether shown below by propylene was carried out as follows.

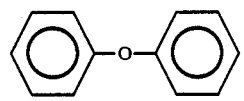

Ten grams of diphenyl ether, 0.5 gram of the catalyst and 10 grams of tridecane as a solvent were charged in an autoclave, and further propylene was introduced untile the total pressure became about 20 kg/cm$^2$G at room temperature. Thereafter, the temperature was raised to 250° C., and the reaction mixture was stirred at 700 rpm to carry out the reaction for 5 hours.

The results are shown in Table 5.

COMPARATIVE EXAMPLE 6

The isopropylation reaction of diphenyl ether was carried out as in Example 14 except that the fluorine-treated H-type mordenite was replaced with a commercially available H-type (TSZ-620 available from Toyo Soda) as a catalyst.

The results are shown in Table 5.

TABLE 5

|  | Examples 14 | Comparative Example 6 |
|---|---|---|
| Catalyst | F-treated H-mordenite | H-mordenite |
| Conversion of diphenyl ether (%) | 84.4 | 81.5 |
| Composition of product (mole %) |  |  |
| Monoisopropyldiphenylmethane | 33.0 | 42.3 |
| Diisopropyldiphenylmethane | 56.1 | 44.2 |
| Triisopropyldiphenylmethane | 10.8 | 14.2 |

Examples for producing 4,4'-dihydroxybiphenyl from the 4,4'-diisopropylbiphenyl obtained as described above are described hereinafter.

EXAMPLE 15

Oxidation reaction

Five hundred milliliter Hastelloy B autoclave equipped with a stirrer, gas-blowing tube, reflux condenser and reaction solution-sampling inlet was charged with 100 grams of 4,4'-diisopropylbiphenyl(4,4'-DIPBP) as a starting material, 178 grams of 4.5 weight % aqueous NaOH solution and 0.5 gram of azobiscyclohexanecarbonitrile as an initiator. This reaction vessel was installed in an oil bath adjusted to a temperature of 100° C., and stirring of the reaction solution (1500 rpm) and blowing of air (20 Nl/hour) were initiated. The reaction was initiated under a pressure of 5 kg/cm$^2$G, and carried out for 12 hours. As a result, the conversion of 4,4'-DIPBP was 99.7%; the yield of DHP was 16.7 mole %; the yield of HHP was 41.0 mole %; the yield of DC was 18.0 mole %; the yield of MHP was 7.3 mole %; and the yield of MC was 5.0 mole %;

EXAMPLE 16

Example 15 was repeated except that the amount of the aqueous NaOH solution was changed from 178 grams to 100 grams. The reaction results obtained by carrying out the reaction for 12 hours were as follows: the conversion of 4,4'-DIPBP was 99.2%; the yield of DHP was 18.3 mole %; the yield of HHP was 36.6 mole %; the yield of DC was 18.2 mole %; the yield of MHP was 9.3 mole %; and the yield of MC was 6.8 mole %.

EXAMPLE 17

Example 16 was repeated except that the concentration of the aqueous NaOH solution was changed from 4.5% by weight to 2.25% by weight. The reaction results obtained by carrying out the reaction for 17 hours were as follows: the conversion of 4,4'-DIPBP was 97.8%; the yield of DHP was 31.5 mole %; the yield of HHP was 26.4 mole %; the yield of DC was 4.5 mole %; the yield of MHP was 23.1 mole %; and the yield of MC was 5.2 mole %.

EXAMPLE 18

Example 17 was repeated except that the amount of the aqueous NaOH solution was changed from 100 grams to 50 grams. The reaction results obtained by carrying out the reaction for 28 hours were as follows: the conversion of 4,4'-DIPBP was 96.8%; the yield of DHP was 27.7 mole %; the yield of HHP was 25.2 mole %; the yield of DC was 4.1 mole %; the yield of MHP was 29.7 mole %; and the yield of MC was 5.5 mole %.

EXAMPLE 19

Example 15 was repeated except that 20 grams of a 2.25% aqueous NaOH solution were charged as an initial charging and thereafter intermittently added as the reaction proceeded. The amount of NaOH added during the reaction of 18 hours was 0.465 time per one mole of 4,4'-DIPBP. The reaction results obtained under such conditions were as follows: the conversion of 4,4'-DIPBP was 99.9%; the yield of DHP was 26.1 mole %; the yield of HHP was 42.3 mole %; the yield of DC was 13.6 mole %; the yield of MHP was 2.9 mole %; and the yield of MC was 1.3 mole %.

EXAMPLE 20

Acid cleavage

An oxidation reaction mixture having the following composition was used to carry out its acid cleavage reaction:

| MHP | 2.1% by weight | MC | 1.6% by weight |
|---|---|---|---|
| DHP | 7.8% by weight | HHP | 13.1% by weight |
| DC | 5.9% by weight | KC | 1.3% by weight |
| KHP | 1.6% by weight | DK | 0.1% by weight |
| MIBK | 66.5% by weight |  |  |

A 300 milliliter flask equipped with a condenser was charged with 0.10 gram of sulfuric acid and 9.5 grams of acetone, and the mixture was heated under reflux. Then, a starting solution obtained by mixing 55.5 grams of the acid reaction mixture as described above, 27.8 grams of acetone and 3.6 grams of 60% aqueous hydrogen peroxide was all fed to a flask over 1.5 hour by means of a feed pump. After feeding was completed, the reaction was continued for further 2 hours at a temperature of 69° C.

The conversion of hydroperoxide was 98.1%, and the yield of 4,4'-dihydroxybiphenyl was 85.8%.

EXAMPLE 21

A flask similar to that described in Example 20 was charged with 0.05 gram of sulfuric acid and 9.6 grams of acetone, and the mixture was heated under reflux. A starting solution obtained by mixing 55.5 grams of the some oxidation reaction mixture as that described in Example 20, 27.6 grams of acetone and 3.6 grams of 60% aqueous hydrogen peroxide was all fed to a flask over 1.5 hour by means of a feed pump. After feeding was completed, the reaction was continued for further 3 hours at a temperature of 69° C.

The conversion of hydroperoxide was 97.3%, and the yield of 4,4'-dihydroxybiphenyl was 84.0%.

EXAMPLE 22

A flask similar to that described in Example 20 was charged with 0.20 gram of sulfuric acid and 19.1 grams of acetone, and the mixture was heated under reflux. A starting solution obtained by mixing 55.5 grams of the same oxidation reaction mixture as that described in Example 20, 17.9 grams of acetone and 3.6 grams of 60% aqueous hydrogen peroxide was all fed to a flask over 1.5 hour by means of a feed pump. After feeding was completed, the reaction was continued for further 2 hours at a temperature of 69° C.

The conversion of hydroperoxide was 99.3%, and the yield of 4,4'-dihydroxybiphenyl was 86.4%.

Examples for producing diacyloxybiphenyls from the 4,4'-diisopropylbiphenyl as described above are described.

EXAMPLE 23

A 5 liter autoclave equipped with a rotatable stirrer, gas-blowing tube, alkali-feeding tube and thermometer sheath and reflux condenser was charged with 1100 grams of 4,4'-diisopropylbiphenyl (4,4'-DIPBP), 550 grams of 4.5 weight % aqueous NaOH solution, 650 grams of $H_2O$ and 5.5 grams of 4,4'-diisopropylbiphenyl hydroperoxide obtained by previously oxidizing 4,4'-DIPBP to use as an initiator. The reaction was carried out at a reaction temperature of 100° C. under a reaction pressure of 6 kg/cm$^2$G with stirring at a stirring rate of 1000 rpm while passing air at a flow rate of 195 Nl/hr. At reaction initiation, 10 weight % aqueous NaOH solution was fed. After 26 hours, the reaction was stopped. The amount of the 10 weight % aqueous NaOH solution fed during the process was 564 cubic centimeters (NaOH/4,4'-DIPBP=0.47 equivalent/mole). After the reaction was completed, the autoclave was opened, the contents were removed. After 2200 grams of methyl isobutyl ketone (MIBK) were added to the resulting oxidation reaction mixture, the oil phase (the MIBK phase) and the aqueous phase were separated. The oxidation reaction product contained in this oil phase was analyzed by liquid chromatography to know the followings.

| DHP | 10.4% by weight | HHP | 15.9% by weight |
| --- | --- | --- | --- |
| DC | 4.8% by weight | MHP | 1.0% by weight |
| MC | 0.4% by weight | | |

Other products (their molecular weights are considered to be 238) were 4.4% by weight. As a result, the conversion of 4,4'-DIPBP was at least 99%; the yield of DHP was 26 mole %; the yield of HHP was 42 mole %; the yield of DC was 14 mole %; the yield of MHP was 3 mole %; and the yield of MC was 1 mole %.

(2) A 2 liter glass reaction vessel equipped with a rotatable stirrer, reflux condenser, tube for feeding acid decomposition starting materials and tube for feeding acid catalyst solutions was charged with 84.9 grams of an acetone solution containing 1.7 weight % $H_2SO_4$, and this reaction vessel was placed on a hot water bath at a temperature of 65° C. When acetone started to reflux by heating, a mixture of 708 grams of the MIBK solution of the oxidation product obtained in (1) described above, 67 grams of 60% aqueous hydrogen peroxide and 219 grams of acetone was started to be fed from the tube for feeding the acid decomposition starting material. At the same time as the feed initiation of this acid decomposition starting material, 129 grams of an acetone solution containing 1.7% $H_2SO_4$ was started to be fed from the tube for feeding acid catalyst solutions. After one hour, feeding was discontinued. The amounts of the decomposition starting material and acetone solution containing $H_2SO_4$ fed were determined by means of a miniature measuring pump. Thereafter, the reaction was carried out for further 3 hours.

The acid cleavage reaction described above was carried out twice, and the resulting reaction mixtures were combined. As a result of liquid chromatography analysis, the acid cleavage reaction product contains the following:

| | |
| --- | --- |
| Acetone | 43.3% by weight |
| MIBK | 37.2% by weight |
| 4,4'-Dihydroxybiphenyl | 11.9% by weight |
| 4-Isopropyl-4'-hydroxybiphenyl | 0.7% by weight |
| Other products (molecular weights are considered to the same as that of 4-isopropyl-4'-hydroxybiphenyl) | 2.6% by weight |
| Water | 4.0% by weight |

(3) Of the acid cleavage reaction mixture described above, 2000 grams were then taken, and, in order to neutralize $H_2SO_4$ contained therein, 2% aqueous sodium carbonate solution was gradually added until the pH of the solution became about 4. Thereafter, in order to remove acetone and MIBK contained in the acid decomposition reaction mixture, the following concentration operation was carried out.

First, acetone was distilled off under atmospheric pressure on a rotary evaporator to obtain an aqueous phase and an oil phase (two liquid phases), and the oil phase and the aqueous phase were separated. The separated oil was again treated under reduced pressure (from 20 to 30 mm Hg) on a rotary evaporator to distill MIBK off to obtain a concentrate. This concentrate contained 78.2% by weight of 4,4'-dihydroxybiphenyl and 4.5% by weight of 4-isopropyl-4'-hydroxybiphenyl.

To 40 grams of this concentrate were added 150 grams of cumene, and 46 grams of acetic anhydride were added. Sulfuric acid was dropwise added with stirring until the concentration of sulfuric acid in the system was 500 ppm. The reaction mixture was raised to 130° C. The reaction solution was started to reflux and the reaction was carried out for one hour, thereafter the reaction solution was allowed to be cooled. After the reaction solution was cooled to 20° C., the crystal and the filtrate were separated, and the reaction yield and the crystal recovery yield were determined from the content of each diacetoxybiphenyl (4,4'-DAB). As a result, the reaction yield was 99 mole % (on a 4,4'-DHB basis), the crystal recovery yield was 95 mole %, and the purity was 99.5%.

EXAMPLE 24-26

The concentrate obtained in Example 23 was used to carry out the reaction as in Example 23 except that cumene was replaced with acetone, methyl isobutyl ketone (MIBK), or acetic acid respectively. The results are shown in Table 6.

TABLE 6

| Examples | Solvents (150 g) | Reaction temperature (°C.) | Reaction yield (%) | Crystal recovery yield (%) | Purity (%) |
| --- | --- | --- | --- | --- | --- |
| 24 | aceton | 60 | 99.2 | 90 | 99.6 |

TABLE 6-continued

| Examples | Solvents (150 g) | Reaction temperature (°C.) | Reaction yield (%) | Crystal recovery yield (%) | Purity (%) |
|---|---|---|---|---|---|
| 25 | MIBK | 130 | 99.7 | 95 | 99.6 |
| 26 | acetic acid | 130 | 99.5 | 96 | 99.4 |

EXAMPLE 27

One hundred grams of the unneutralized acid decomposition product obtained in Example 23 were charged into a 300 milliliter glass reaction vessel equipped with a rotatable stirrer, reflux condenser and dropping funnel, and this reaction vessel was placed on a hot water bath at a temperature of 65° C. When acetone started to reflux by heating, dropping of acetic anhydride was started. After 20 grams of acetic anhydride were dropwise added over one hour, the reaction was carried out for 130 minutes at a temperature of 60° C. As a result of liquid chromatography analysis, the concentration of 4,4'-diacetoxybiphenyl (4,4'-DAB) was 11.9% by weight. The yield of 4,4'-DAB (on a DHB basis) was 99.7 mole %. Acetone was distilled off from this reaction solution, and the reaction solution was allowed to be cooled to 20° C. Thereafter, the crystal and the filtrate were separated. As a result, the crystal recovery yield was 87%, and the purity was 99.3%.

EXAMPLE 28

The neutralized acid cleavage product obtained in Example 27 (200 grams) was used. First, acetone was distilled off and the oil phase (the MIBK phase) containing the following ingredients and the aqueous phase were separated.

| Ingredients of MIBK Solution | |
|---|---|
| MIBK | 70.5% by weight |
| DHB | 22.5% by weight |
| MHB | 1.3% by weight |
| Other products | 5.7% by weight |

Some water contained in the oil phase was removed by azeotropic distillation to obtain an MIBK solution, and this MIBK solution (50 grams) and 16.6 grams of acetic anhydride were added to a 300 milliliter glass reaction vessel equipped with a rotatable stirrer, reflux condenser and dropping funnel. Sulfuric acid was dropwise added with stirring until the concentration of sulfuric acid in the system was 500 ppm. The reaction mixture was raised to 130° C. The reaction was started to reflux, and the reaction was carried out for one hour. Thereafter, liquid chromatography analysis was carried out. As a result, the concentration of 4,4'-DAB was 24.5% by weight, and the yield of 4,4'-DAB was 99.7 mole %. This reaction solution was allowed to be cooled to 20° C., and thereafter the crystal and the filtrate were separated. The crystal recovery yield and purity were determined. As a result, the recovery yield was 91 mole %, and the purity was 99.2%.

What is claimed is:

1. A process for producing a dialkyl-substituted aromatic hydrocarbon which comprises the step of reacting (i) an aromatic hydrocarbon with (ii) an alkylating agent selected from the group consisting of olefins, lower aliphatic alcohols and alkyl halides in the presence of a mordenite zeolite catalyst treated with a fluorine-containing compound selected from the group consisting of an aqueous ammonium fluoride solution, chlorofluorocarbons, fluorohydrocarbons, chlorofluorohydrocarbons, bromofluorocarbons, perfluorocarbons, $SF_4$, $SF_6$ and $BF_3$.

2. The process according to claim 1 wherein the aromatic hydrocarbon (i) is biphenyl, diphenylmethane or naphthalene.

3. The process according to claim 1 wherein the alkylating agent (ii) is propylene.

4. The process according to claim 1 wherein the resulting alkyl group-substituted aromatic hydrocarbon is p,p'-diisopropylbiphenyl.

5. The process according to claim 1, wherein the aromatic hydrocarbon (i) is benzene; monoalkyl benzene; biphenyl; biphenyls having one or two substituents selected from the group consisting of methyl, ethyl, isopropyl, phenyl, chloro, methoxy and acetyl; naphthalene; naphthalenes having one or more substituents selected from the group consisting of methyl, ethyl, isopropyl, methoxy, acetyl and halogen; diphenyl ether; diphenyl ethers having one or more substituents selected from the group consisting of methyl, ethyl, isopropyl, halogen, methoxy and acetyl; diphenylmethane; diphenylethane; diphenylpropane; or diphenylalkanes having one or more substituents selected from the group consisting of methyl, ethyl, propyl, halogen and acetyl.

6. The process according to claim 1, wherein the alkylating agent (ii) is an olefin.

7. The process according to claim 6, wherein the olefin is selected from the group consisting of ethylene, propylene, n-butene, isobutene, octene, decene, cyclopentene, cyclohexene and isoamylene.

8. The process according to claim 1, wherein the alkylating agent (ii) is an aliphatic alcohol.

9. The process according to claim 8, wherein the aliphatic alcohol is selected from the group consisting of ethanol, propanol, n-butanol, isobutanol, tertiary-butanol, cyclopentanol, cyclohexanol and dodecyl alcohol.

10. The process according to claim 1, wherein the alkylating agent (ii) is an alkyl halide.

11. The process according to claim 10, wherein the alkyl halide is selected from the group consisting of methyl chloride, methyl iodide, ethyl chloride, ethyl iodide, propyl chloride, propyl iodide, dodecyl chloride, butyl chloride, benzyl chloride and chlorotoluene.

12. The process according to claim 1, wherein said chlorofluorocarbons are selected from the group consisting of $CFCl_3$, $CF_2Cl_2$, $CF_3Cl$, $CFCl_2-CFCl_2$, $CF_2Cl-CF_2Cl$ and $CF_2Cl-CF_3$.

13. The process according to claim 1, wherein said fluorohydrocarbons are selected from the group consisting of $CHF_3$ and $CH_3-CHF_2$.

14. The process according to claim 1, wherein said chlorofluorohydrocarbons are selected from the group consisting of $CHFCl_2$ and $CHF_2Cl$.

15. The process according to claim 1, wherein said bromofluorocarbons are selected from the group consisting of $CF_3Br$ and $CF_2Br-CF_2Br$.

16. The process according to claim 1, wherein said perfluorocarbons are selected from the group consisting of $CF_4$, $CF_3-CF_3$ and $(CF_2-CF_2)_2$.

* * * * *

UNITED STATES PATENT AND TRADEMARK OFFICE
CERTIFICATE OF CORRECTION

PATENT NO. : 4,891,465
DATED : January 2, 1990
INVENTOR(S) : KATSUO TANIGUCHI ET AL.

It is certified that error appears in the above-identified patent and that said Letters Patent is hereby corrected as shown below:

On the cover page, in the title, "PRODUCTING" should read --PRODUCING--.

Signed and Sealed this

Nineteenth Day of February, 1991

Attest:

HARRY F. MANBECK, JR.

*Attesting Officer*     *Commissioner of Patents and Trademarks*